United States Patent
Horvath et al.

(10) Patent No.: US 6,648,642 B1
(45) Date of Patent: Nov. 18, 2003

(54) RUBBER DAM

(75) Inventors: Domonkos Horvath, Bahnhofstrasse 24, D-79798, Jestetten (DE); Felix Lutz, Meilen (CH)

(73) Assignee: Domonkos Horvath, Jestetten (DE)

( * ) Notice: Subject to any disclaimer, the term of this patent is extended or adjusted under 35 U.S.C. 154(b) by 0 days.

(21) Appl. No.: 09/355,059

(22) PCT Filed: Nov. 26, 1997

(86) PCT No.: PCT/IB97/01480

§ 371 (c)(1), (2), (4) Date: Sep. 24, 1999

(87) PCT Pub. No.: WO98/34559

PCT Pub. Date: Aug. 13, 1998

(30) Foreign Application Priority Data

| Feb. 10, 1997 | (DE) | 197 04 904 |
| May 28, 1997 | (DE) | 197 22 218 |
| Aug. 4, 1997 | (DE) | 197 33 712 |

(51) Int. Cl.$^7$ .................................................. A61C 5/12
(52) U.S. Cl. ..................................................... 433/136
(58) Field of Search ................. 433/136, 137, 433/138, 139

(56) References Cited

U.S. PATENT DOCUMENTS

| 174,942 A | * | 3/1876 | Brown | |
| 2,680,908 A | * | 6/1954 | Daigle | 433/136 |
| 3,772,790 A | * | 11/1973 | Swan-Gett et al. | 433/136 |
| 3,781,994 A | * | 1/1974 | Hesselgren | 433/137 |
| 4,639,221 A | * | 1/1987 | Sairenji | 433/139 |
| 4,664,628 A | * | 5/1987 | Totaro | 433/136 |
| 4,695,253 A | * | 9/1987 | Tysse | 433/136 |
| 4,934,382 A | * | 6/1990 | Barone, Jr. | |
| 5,011,409 A | | 4/1991 | Gray | 433/136 |
| 5,078,604 A | | 1/1992 | Malmin | 433/138 |
| 5,340,313 A | | 8/1994 | Hussin | 433/136 |
| 5,433,221 A | * | 7/1995 | Adair | |
| 5,499,917 A | | 3/1996 | Erickson et al. | 433/137 |
| 5,669,770 A | * | 9/1997 | Fisher et al. | 433/137 |

FOREIGN PATENT DOCUMENTS

EP          0 294 230 A1     6/1988

* cited by examiner

Primary Examiner—Ralph A. Lewis

(57) ABSTRACT

The rubber-dam preferably has bag shape or it can be brought into bag shape by means of suited holder means, such that it can be well placed into the oral cavity. On its forward end it is rolled up and stretched onto a rubber-dam frame. The cover means of the rubber-dam can be cut open in the operating field. For sealing against gingiva, dental clips or teeth, it is provided with a glue coating or is suited for receiving an adhesive, respectively. The rubber-dam is easy to install, allows to isolate teeth and adjacent gingiva and requires no affixing clips traumatizing the teeth.

27 Claims, 6 Drawing Sheets

RUBBER DAM

CROSS REFERENCES TO RELATED APPLICATIONS

This application claims the priority of the German patent applications 197 04 904 4, 197 22 218 8 and 197 33 712.0, filed on Feb. 10, 1997, May 28, 1997 and Aug. 4, 1997, and the disclosure of which is incorporated herein by reference in its entirety.

TECHNICAL FIELD

The invention relates to a rubber-dam and a method according to the preamble of the independent claims.

In dentistry, a rubber-dam is an aid for dental treatments that allows an isolation and thereby to keep the teeth to be treated dry. By this isolation the danger of infection in the area of the treated tooth is reduced as well. Synonymous terms are rubber dam, stretching rubber (Spanngummi), rubber flap (Gummilappen), rubber plate (Gummiplatte), rubber cloth (Gummituch), etc.

STATE OF THE ART

Since the year 1864 it has been known to puncture a rubber cloth and to pull it over the tooth such that the edge of the hole in the rubber cloth abuts on the hard tooth and the rubber cloth covers the oral mucosa while the upper part of the tooth remains treatable. For better attaching the rubber-.foil to the teeth various means have been proposed. Most widely propagated are, however, metal clamps that affix the rubber cloth to the tooth.

Even though the rubber-dam could be of largest significance for modern dental treatments, it is only seldom used by dentists.

DISCLOSURE OF THE INVENTION

Hence, it is a task of the invention to further develop a rubber-dam and the method according to the preamble, which lives up to the grown requirements of the dental practice.

In one aspect of the invention, this task is solved by the rubber-dam. The cover means hence is substantially bag-shaped, i.e. it is pre-shaped like a bag. In contrast to known embodiments, where the cover means is formed by a planar-foil, the rubber-dam according to the invention can be mounted in the oral cavity without strong deformation. Thereby, the application is made easier and lower retaining forces are required for affixing.

For sealing the rubber-dam against the hard dental material, soft tissue or affixing devices it can be provided with adhesive areas.

Since affixing the rubber-dam requires small retaining forces only, affixing is made easier and conventional attaching clamps, which can damage the teeth, are not required. Instead of this, it becomes possible to uncover not only the teeth but also the gingiva in the working area, such that the neck of the tooth and the adjacent gingiva become accessible for treatment by the dentist. This is of central importance for modern dental treatment.

It is advantageous to use a holder means, by means of which the cover means can be pushed against the oral cavity. This improves sealing and results in even lower forces in a possible adhesive area.

In another aspect of the invention the rubber-dam comprises a cover means and an affixing device, wherein the affixing device comprises a holder means that is firmer than the cover means and connected to the cover means and which can be set against the gingiva on both sides of the dental row in the oral cavity, for commonly isolating tooth and gingiva. In this case, the cover means does not necessarily have to be bag shaped in its relaxed state.

This embodiment of the invention is based on the finding that the conventional rubber-dam affixed to the tooth necessarily covers a lower area of the teeth and therefore substantially limits the dry working field. Treatments in the area of the gingival margin are hardly possible or only under traumatization of the marginal sulcus. Treatments that involve the gingiva cannot be carried out with the known rubber-dam at all. The rubber-dam according to the invention, however, allows to maintain the tooth neck and the adjacent gingiva as an inseparable unit of treatment for the dentist and to isolate a dento-gingival unit from the oral cavity.

The affixing device lays the cover means against the gingiva on both sides of the dental row and therefore leaves enough room in the area of the teeth for cutting out an opening, which provides access to the tooth or teeth to be treated as well as the gingiva around them. In the jaw area to be treated, the restoration margin and marginal gingiva are therefore laid open as a treatment unit, wherein the firmer holder means extends around this treatment unit for laying the cover means against the gingiva.

It is advantageous if a gluing or adhesive area, respectively, is arranged in the area of the holder means. If only a retention function is required, this gluing area can be dispensed with. However, in order to reach good protection against infections and humidity, a reversible gluing zone is proposed for attaching the over means in the area of the humid oral cavity. Glues hat have proved to be suited for slightly wetted mucosa re e.g.: Pectin, gelatine, sodium carboxyl cellulose, olyisobutylene, calcium-sodiumalginate, hydrocolloid-compounds, polyvinyl acetate and carboxyl methyl celluose, etc. The gluing area is located preferably at least also on the holder means or on the side of the cover means opposite to the holder means, depending on which side of the cover means the holder means is arranged.

It is especially favorable if the area of the over means lying between the holder members arranged on both sides of the row of teeth is used as gluing area. This area can be positioned against the gingiva without any pressure and the flexibility of the cover means allows a simple adaptation to irregularities in the gingival region.

In order to optimally adapt the holder means to the individual anatomy, it is proposed that the holder means is plastically deformable. The firmness is then chosen such that an adaptation to the individual gingival shape, without pressure to the gingiva, is guaranteed.

The holder means can, however, also be elastic. An anatomically adapted form of the holder means is in this case produced from an elastic material, for being versatile and for exerting a slight pressure to the gingiva without injuring adjacent tissue.

In addition to this, the holder means can comprise plastic and elastic sections at the same time, e.g. for being plastically adaptable against the gingiva parallel to the tooth row and being elastic transversely to the tooth row for holding the plastic sections against the gingiva.

A preferred embodiment provides that the holder means is arranged around an opening in the cover means. In this way, a frame is created that, in practice, surrounds the treated tooth area and lays the cover means against the gingiva.

Since the tooth rows have arc shape, it is proposed that the holder means comprises two concentric arc members arranged at a distance from each other. This allows to place one arc member of the holder means from S within and the other from without the tooth row against the gingiva.

U-shaped arc members allow the isolation of the complete upper or lower jaw.

It is further proposed that the holder means comprises two concentric ring members arranged at a distance from each other. These ring members can be introduced into the oral cavity in such a way that they form two U-shaped arc members for uncovering the upper and the lower jaw. In this case it is advantageous if the ring members are separated by buckling points on opposite sides of the ring into U-shaped arc members.

When arc or ring members are used, it is advantageous to provide a gluing area between the arc or ring members, respectively. This gluing area allows a good isolation in the area of the opening in the cover means, as well as an adaptation between holder means and gingiva.

To allow an attachment of the cover means to the tooth row in addition the holder means while avoiding the known, clawed, traumatizing rubber-dam clamps, it is proposed that the affixing device comprises truly and anatomically shaped, non-traumatizing plastic clips that can be pushed over the tooth, either applied directly onto the tooth with the cover means thereon or vice versa, in each case sealed by an adhesive. These clips are adequately soft such that they do not damage the tooth and can also abut on the gingiva. These clips can also be connected to the holder means and stabilize the latter.

Further it is proposed that the rubber-dam according to the invention comprises a rubber-dam frame, which is arranged circularly around the affixing device. A so-called perioral frame stabilizes the cover means on the outside and preferably extends circularly around the upper and lower lip. This rubber-dam frame is preferably adaptable such that it does not disturb the dentist or patient, e.g. by being radially extendible.

In a further preferred embodiment at least one groove is arranged in an incisal/occlusal area of the cover means, which marks the place where the rubber-dam must be cut open in order to gain access to the corresponding teeth. In this way, an accurate opening of the cover means becomes possible.

BRIEF DESCRIPTION OF THE DRAWINGS

Further advantages and applications of the invention result from the dependent claims and the now following description referring to the figures. Herein show:

MODES FOR CARRYING OUT THE INVENTION

Figure 1:
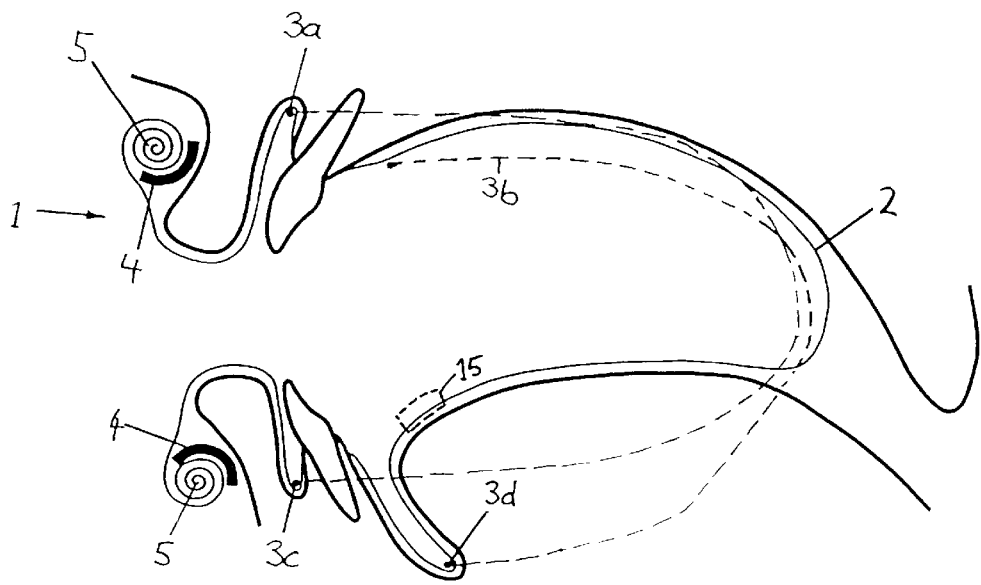
FIG. 1 a sagittal section of the oral cavity with a first embodiment of the rubber-dam according to the invention, FIG. 2 a frontal section of the oral cavity with the rubber-dam of FIG. 1, FIG. 3 an enlarged detail of FIG. 2 with a cover means that has not been cut open in the area of the upper molars, FIG. 4 a view of the cover means cut open, FIG. 5 a view of the cover means cut open in free end situation, FIG. 6 a sagittal section of a second embodiment of the rubber-dam, FIG. 7 a frontal section of the rubber-dam of FIG. 6, FIG. 8 a third embodiment of a rubber-dam according to the invention, FIG. 9 a fourth embodiment of a rubber-dam according to the invention, FIG. 10 a fifth embodiment of a rubber-dam according to the invention, FIG. 11 a plastic clip for being used with a rubber-dam according to the invention, FIG. 12 a second embodiment of a plastic clip, FIG. 13 a third embodiment of the plastic clip, FIG. 14 an alternative to the embodiment of FIGS. 1–3, and FIG. 15 the embodiment of FIG. 14 in cut open state.
Figure 2:
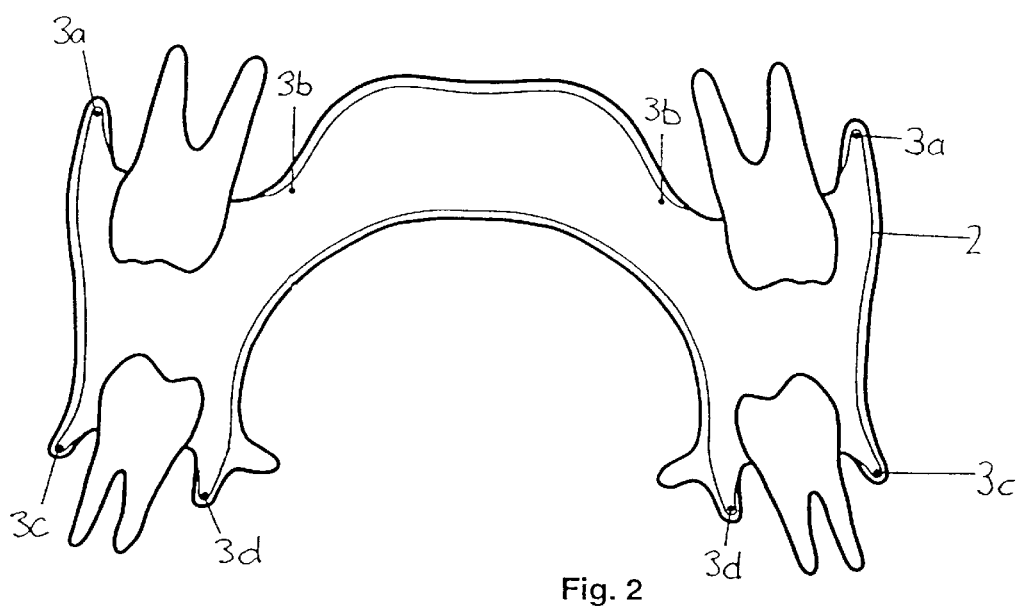

A first, presently preferred embodiment of the rubber-dam 1 according to the invention is shown in FIGS. 1 and 2. It consists of a cover means 2 and an attachment device 3*a*–3*d* forming a holder means. The cover means 2 is a foil of raw latex, e.g. of cis-1,4 polyisoprene. Other materials can, however, be used as well, e.g. PVC or silicon. The cover means is three-dimensionally pre-shaped and has substantially the shape of a bag adapted to the anatomy of the oral cavity. Without having to be deformed, it can be introduced deeply into the oral cavity.

In the embodiment shown here, the affixing device comprises four arc shaped retaining members. 3*a*–3*d*, which are either integrated into the cover means 2 or introduced into the oral cavity after application of the rubber-dam. The retaining members 3*a*–3*d* are made of a firmer material than the cover means. The two retaining members 3*a*, 3*c* extend buccally in the upper or lower vestibules of oral cavity, the retaining members 3*b* and 3*d* push the cover means 2 orally against the oral cavity. This causes the cover means 2 to abut in the area between the retaining members 3*a*–3*d*, i.e. in the area of the teeth, substantially without forces applied thereto.

The retaining members 3*b* and 3*d* are connected to each other in an arc shape, in the same way as the retaining members 3*a* and 3*c*, as it is indicated with dashed lines in FIG. 1, such that they are able to generate vertical tensional forces. It is also conceivable that retaining members 3*a* and 3*d* are connected in an arc, and also retaining members 3*b* and 3*c*, such that the upper jaw's vesticular arc is connected to the lower jaw's lingual arc. In the two points where the pair of arcs cross, they are buckled and articulately affixed to each other.

If desired, the upper arcs can be releasably connected to the corresponding lower arcs, e.g. by being able to be plugged into each other. In this way, the arcs can be detached from each other such that the rubber-dam can be folded compactly.

A rubber-dam frame 4, which encloses, in frontal view, the lips, is arranged outside the mouth. It forms a trough where the outer margin 5 of the cover means 2 is rolled up. The rolled up foil material serves as a material reserve, such that the depth of the rubber-dam can be adapted to the individual requirements. The rubber-dam frame 4 has an oval, perioral shape. It is held by the rolled up rubber-dam margin. The rubber-dam frame is preferably extendible, such that better access to the interior of the rubber-dam becomes possible. For this purpose, it can e.g. consist of two parts with two half arcs. In the joints between the half arcs accordion-like folds are provided in the cover means as spare material.

In the lower jaw area of the cover means there is an opening 15, which can be opened and closed reversibly. It serves for receiving a salvia suction tube.

Before application the cover means 2 forms a bag that is closed laterally and at its end. Before being used, it is cut open in those areas that are to be accessible. In FIGS. 1 and 2, the rubber-dam is cut open in the area of all teeth.

Figure 3:
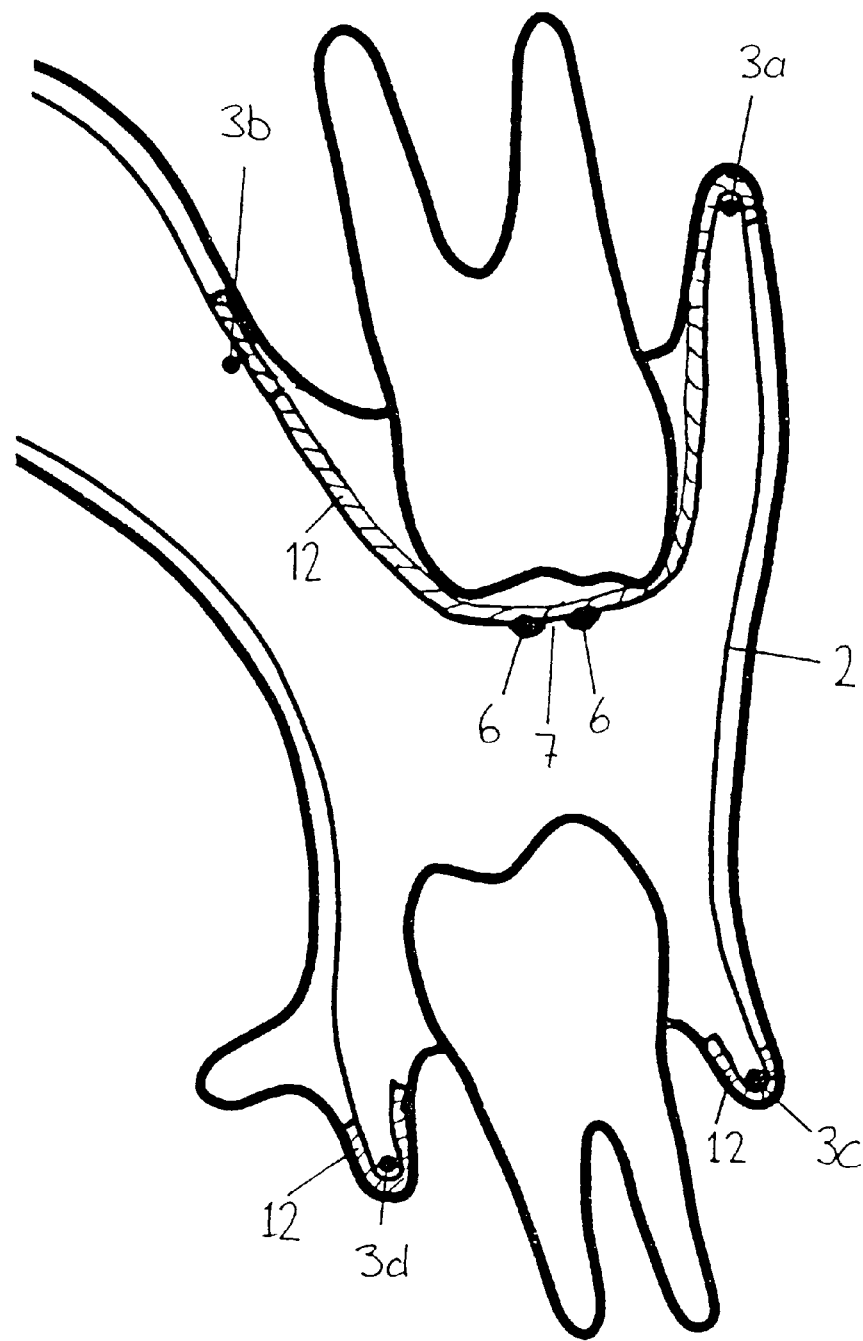

FIG. 3 shows a detail of FIG. 2, wherein here the rubber-dam has not been cut open in the area of the upper molar. The cover means therefore covers the upper molar.

Two parallel veins extend in the cover means along the occlusal area of the teeth, between which a incisal/occlusal groove 7 is formed. This groove 7 marks the position where the cover means must be cut open for making the teeth accessible.

Figure 4:
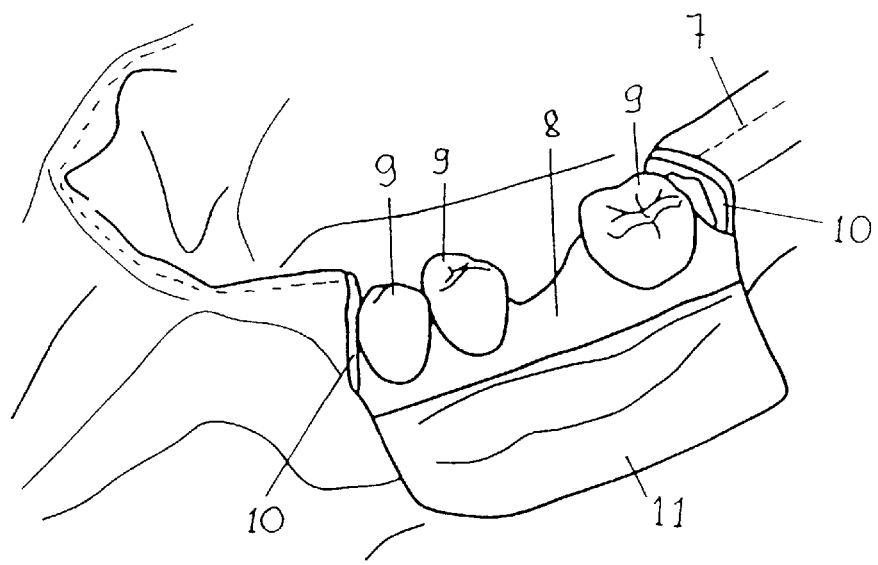

FIG. 4 shows a view of the cut open rubber-dam in the area of a tooth gap 8, wherein three neighboring teeth 9 have also been uncovered. A clip 10 has been positioned on each of the two neighboring teeth. (Preferably, the clips are positioned on top of the cover means.) These are plastic clips, which are adhesively connected to the corresponding tooth by means of a suited cement and provided lingually, occlusally and bucally with flat adhesion surfaces. They are connected to the cover means 2 by means of a gluing layer and form mesial and distal seal of the operation area. In the operation area, the cover means 2 has been cut open with a T-cut along groove 7 and adjacent to clips 10 and folded down. The flaps 11 formed in this way can, if required, be cut off fully. In this way, the clinical crowns together with the adjacent coronal sections of the alveolar ridge and, if required, not only the attached gingiva but also the mobile mucosa can be uncovered.

The lingual and buccal sealing of the operation area is achieved by gluing the corresponding edges of the cover means 2 to the gingiva. For this purpose, as it is in particular shown in FIG. 3, the cover means 2 is provided with a glue on its outer side in an adhesive area 12 between the retaining members 3*a* and 3*b* or 3*c* and 3*d*, respectively. Preferably, the adhesive area extends at least from the retaining member to the firm gingiva, since this area is tension free.

The glue establishes an adhesive, reversible, tissue-friendly, optionally swelling bond between gingiva and/or mucosa and the cover means, at least in the area between the position of the four arched retaining members 3*a*–3*d* and the linea girlandiformis, or the tuber area and the tooth-less area of the ascending lower jaw branch and the cover means 2, respectively. It also serves for attaching the cover means 2 to the clips 10 and to the rubber-dam frame or the perioral skin, respectively.

Instead of or in addition to the glue layer on the outer side of the cover means, the clips can also be provided with glue, or a sealing adhesive can be applied to the periphery of the operating area.

Figure 5:
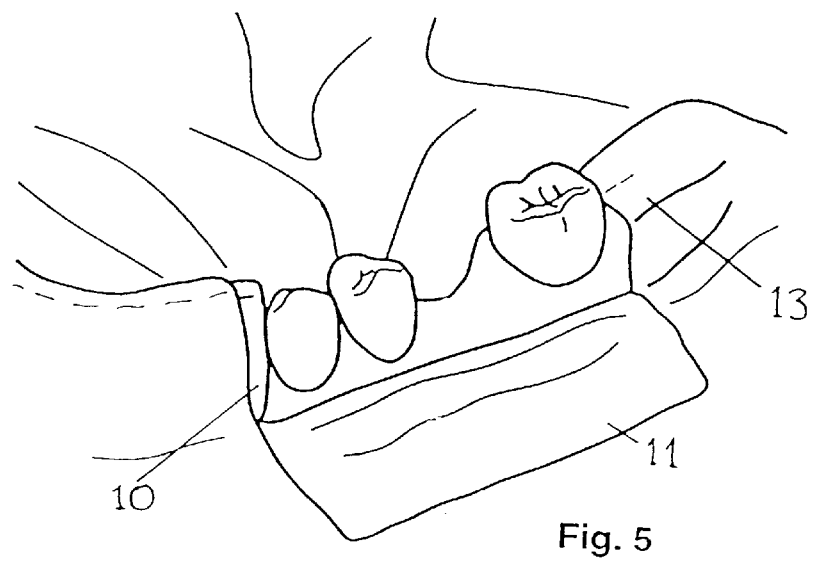

The adhesive area 12 can also form the distal end of the operating area, especially if no tooth for receiving a clip is present in this area. A corresponding situation is shown in FIG. 5. Here, the cover means is glued lingually, occlusally and buccally to the gingiva in the end area 13.

Figure 6:
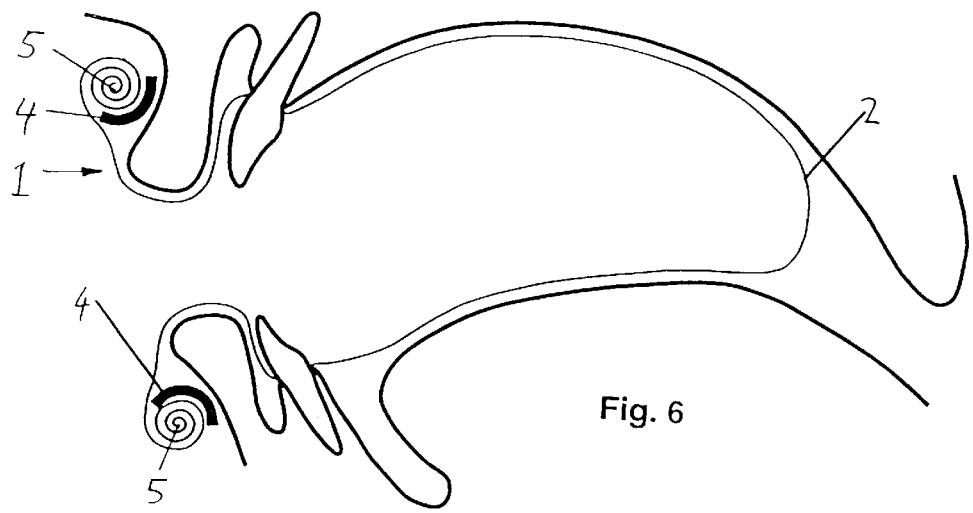
Figure 7:
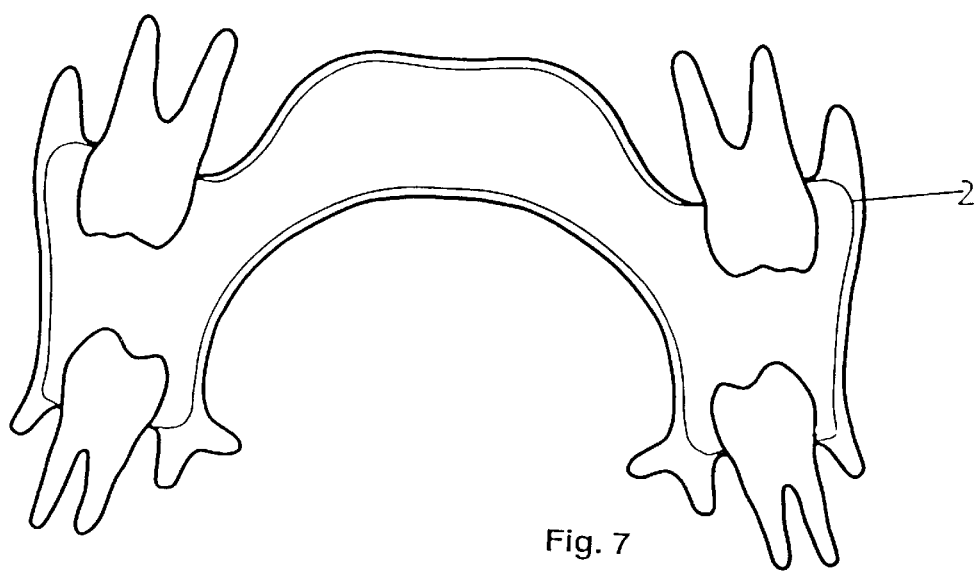

It is also conceivable to dispense with the retaining members 3*a*–3*d*, especially if the shape of the cover means 2 is very well adapted to the inner shape of the oral cavity. A corresponding embodiment is shown in FIGS. 6 and 7. Preferably, also here the outer side of the cover means is provided with a glue layer at least in the area of the gingiva, such that a sufficient sealing can be reached around the operation area and the rubber-dam can be affixed. In the shown embodiment the cover means extends, just like for a conventional rubber-dam, up to the tooth necks.

Figure 8:
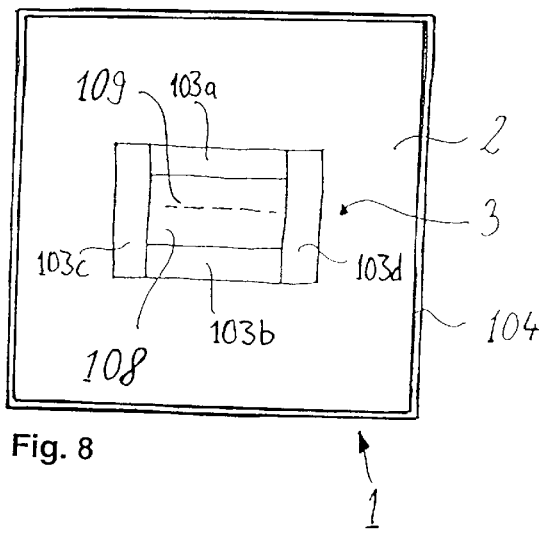

FIG. 8 shows a third embodiment of a rubber-dam 1 according to the invention consisting of a cover means 2 and the affixing device 3. In this case, the cover means 2 is a planar foil made of raw latex or another suited material, which is shown in the figure in its planar state.

The affixing device 3 comprises a frame of two plastically deformable retaining members 103*a* and 103*b* and two elastic connecting members 103*c* and 103*d*, which are applied flat to cover means 2 and serve as a holder means. The frame formed by members 103*a* to d encloses a partial surface 108 of the cover means 2, on which a dotted line 109 with a cut to be applied is drawn. A rubber-dam frame 104 is provided on the outer margin of the cover means 2, which keeps the rubber sheet stretched and can be deformed such that it covers the open mouth area without hampering the dentist or patient.

On the side of the cover means 2 opposite to the holder means 103*a* to d, a glue layer has been applied in the area of the holder means and the limited partial surface 108, which can e.g. exposed by removal of a protective foil.

When using the rubber-dam of FIG. 8, the plastic member 4 and 5 are positioned on both sides of the tooth row to be treated such that the gluing area on the backside of the cover means abuts against the gingiva.

The elastic members 103*c* and 103*d* lie like brackets over the tooth row and keep the members 103*a* and 103*b* in position.

Following this, a such generous cut 109 is applied to the cover means in the partial surface 108 that the teeth as well as the gingiva surrounding the teeth are uncovered. The remaining partial area 108 of the cover means 2 is positioned with the gluing area against the gingiva and forms, together with the holder means 103*a* to d, a tight enclosure of the area of tooth, tooth neck and surrounding gingiva to be treated.

Figure 9:
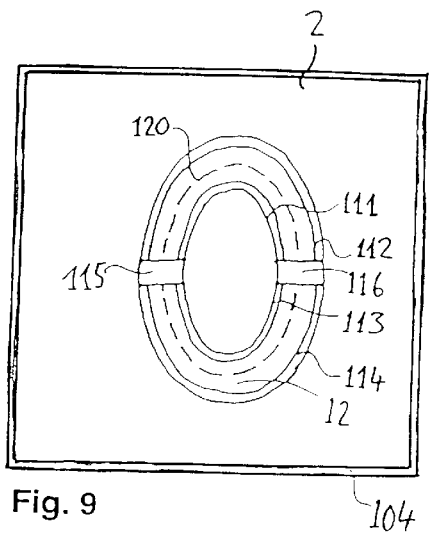

The fourth rubber-dam shown in FIG. 9 can be used universally for treating different areas of the upper and lower jaw. In this embodiment, the holder means is formed by two concentric arc members 111, 112 arranged at a distance from each other, wherein as a mirror image of these, there are two further, concentric arc members 113 and 114 lying at a distance to each other, such that they can also be described as two concentric ring members 111, 113 and 112, 114 arranged at a distance from each other. These arc members are connected to each other by means of buckling points 115 and 116, which allow an easy bending in this area.

A glue area 12 is arranged between the arc members 111, 112 and 113, 114 on the back side of the cover means 2, and a rubber-dam frame 104 extends around the cover means 2 just as in the embodiment of FIG. 8.

When using this fourth rubber-dam, the cover means 2 is placed thus into the oral cavity that the buckling areas 115 and 116 lie in the transitional area between upper and lower jaw. The arc member 111 then lies against the gum on the inner side of the upper tooth row, while the arc member 112 lies against the gingiva in the area of the outer side of the upper tooth row. Correspondingly, arc member 113 lies against the gingiva on the inner side and arc member 114 against the gingiva on the outer side of the lower tooth row. The tooth sections to be treated are uncovered by cutting the cover means 2 in the corresponding places along the dotted line 120, wherein the cut is made such that not only the tooth but also the adjacent gingiva area are uncovered around the tooth section to be treated.

The embodiment of FIG. 9 shows clearly that every tooth section can be treated with a single rubber-dam adapted to the corresponding size of the teeth.

Figure 10:
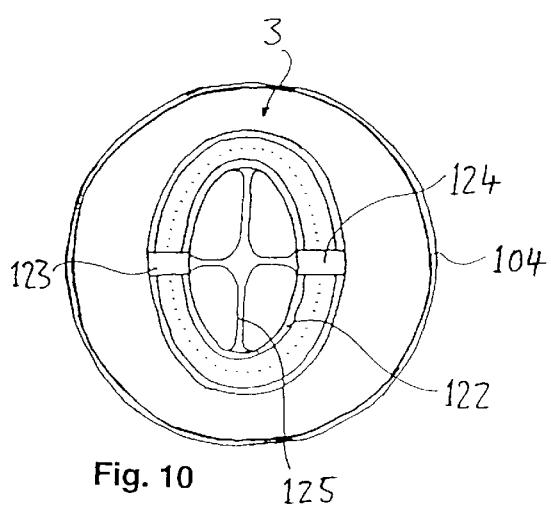

FIG. 10 shows a further development of the rubber-dam of FIG. 1. Here, the rubber-dam frame 104 is circular and its size is such that it extends circularly around upper and lower lip. This has the advantage that the rubber-dam only covers the necessary partial area of the patient's face.

A support member 125 positioned between the buckling positions 123, 124 and supporting the ring member 122 is provided for stabilizing the inner ring member 122, which has cross shape in the embodiment of FIG. 10.

Figure 11:
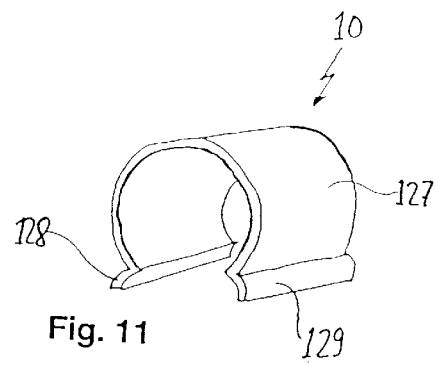

FIG. 11 shows a plastic clip 10 according to the invention that can easily be pushed onto a tooth. The tunnel shaped arc 127 bridges a row of teeth and the holders 128, 129 arranged on its bottom end serve for fastening the clip 126 to the arc members 111 and 112 or 113 and 114.

Figure 12:
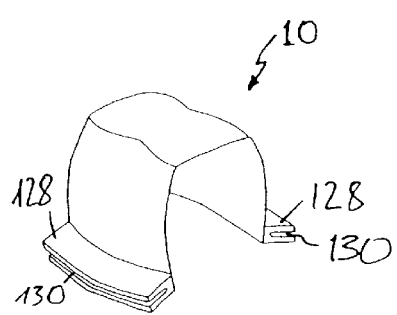

FIG. 12 shows a second embodiment of a plastic clip 10. It is also substantially shaped as a U and comprises holders 128, where notches 130 are formed. The notches 130 serve for receiving the cover means.

The plastic clips 10 of FIG. 11 and 12 are fastened to a tooth by means of a suited cement or glue. However, they can also be shaped such that they can be pushed onto a tooth and hold the same elastically.

Figure 13:
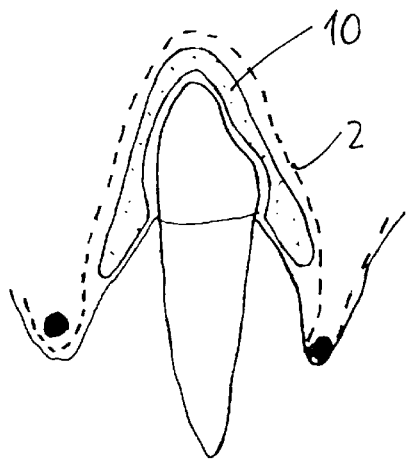

FIG. 13 shows a third embodiment of a clip. This clip is anatomically adapted to the shape of the tooth. It can be prefabricated or consist of a quickly hardening plastic material, which is shaped to the tooth and then hardened. If necessary, a glue can be applied between the clip 10 and the tooth. The cover means is glued to the outer side of the clip.

Figure 14:
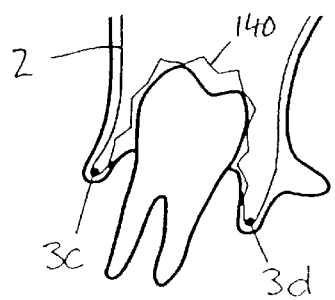
Figure 15:
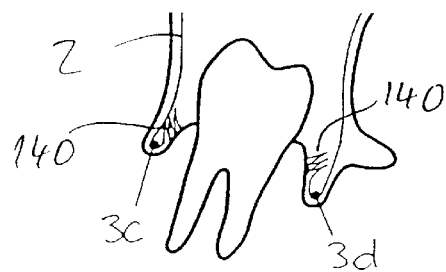

In FIGS. 14 and 15 an alternative embodiment of the cover means 2 is shown. It possesses a bellows area 140 in the area of the tooth rows, which is folded accordion-like. If it is cut open, as shown in FIG. 4, it retracts and releases the operating area.

It is also possible to provide the cover means with a profile, which makes its stretching properties anisotropic. For example, transversal ribs can be formed in the cover means such that the cover means can be stretched better in longitudinal direction than in transversal direction.

Firmness, elasticity and plasticity of the individual members of the rubber-dam according to the invention are to be adjusted such that a sufficiently secure sealing of the tooth area or, if applicable, gingiva area to be treated is reached.

The rubber flap conventionally used for rubber-dam applications can also be replaced by a flexible, substantially inelastic foil, without affecting the function of the rubber-dam. Especially well suited are haptically pleasant or also air permeable foils. Flavorings can be used as well.

The cover means 2 can also be inherently stable, e.g. as an elastic but inherently stable plastic part, such that it can also play the roll of the affixing device 3a–3d.

The rubber-dam can also consist of a flexible foil without affixing device. The foil is flexible and provided with a glue on its whole outer surface. It is glued, similar to a wallpaper, into the oral cavity.

The cover means can also be sold without a glue layer, in which case the user would apply the glue to the mucosa and/or the cover means himself.

Biocompatible substances can be used as a glue, which are suited to increase the force for releasing the cover means from the mucosa. In particular, a viscous adhesive agent can e.g. also be used, which is able to generate a force perpendicular to the cover means while still allowing the cover means to glide on the mucosa.

The rubber-dam according to the invention allows the application of rubber-dam isolation for practically all dental operations. Especially worth mentioning are, among others, the recording of X-ray images, the occlusion control; the preparation of teeth for receiving crowns and veneers, the adhesive attachment of workpieces (dento-gingival isolation), the setting of implants, the recording of individual imprints (dento-alveolar isolation), etc.

The preparation of the operation area including oral structures relevant for treatment into the isolation, and the substitution of strongly traumatizing mechanical forces for affixing the rubber-dam by a broadly contacting, weekly adhesive, tissue friendly isolation of the adjacent gingiva prevents injuries of the gingiva and traumatization of the tooth neck region by conventional affixing devices. Besides "white"-aesthetics (teeth), also the "red"-aesthetics (gingiva) can be judged at any time. The rubber-dam allows a non-traumatizing isolation of the operation area during the whole treatment.

The rubber-dam can also be used for mucosa treatments outside the tooth region, e.g. for the treatment of abscesses.

The application of the rubber-dam can be quick and is tissue-friendly, especially when using a built-in holder means. The system is easy and clear since it only consists of a rubber-dam, a special rubber-dam frame and, if applicable, an adhesive means.

As it is clear for the person skilled in the art, the individual system components shown here (such as e.g. the individual parts of the rubber-dam, the plastic clips and their methods of operation) can be applied individually or in combination. Therefore, the applicant reserves to claim protection for each of these components individually.

While preferred embodiments of the invention are described in the present application, it is to be distinctly understood that the invention is not limited thereto but may also be otherwise embodied within the scope of the following claims.

What is claimed is:

1. A rubber-dam comprising a flexible cover foil for covering an oral cavity of a patient's mouth with upper and lower lips, a frame for being located outside the patient's mouth around the patient's upper and lower lips, wherein said cover foil has, in a relaxed state, the shape of a bag that is closed laterally and at a first end, wherein an outer margin of said cover foil, at a second end opposite the first end, is connected to said frame, and wherein the cover foil comprises on an outer side thereof at least one gluing area provided with an adhesive.

2. The rubber-dam of claim 1, further comprising an affixing device for affixing the rubber-dam in a desired position, wherein said affixing device comprises a holder means for pressing the cover foil against the oral cavity or gingiva or mucosa thereof, wherein the holder means is firmer than the cover foil.

3. The rubber-dam of claim 1 wherein the holder means is connected to the cover foil and arranged for being applied to the gingiva or the mucosa on both sides of a row of teeth for commonly isolating tooth and gingiva.

4. The rubber-dam of claim 1 wherein a gluing area provided with an adhesive is arranged in the area of the holder means.

5. The rubber-dam of claim 1 wherein the holder means is plastically deformable.

6. The rubber-dam of claim 1 wherein the holder means is elastically deformable.

7. The rubber-dam of claim 1 wherein the holder means is arranged around an opening or a mark for an opening in the cover foil.

8. The rubber-dam of claim 1 wherein the holder means comprises two concentric arc members arranged at a distance from each other.

9. The rubber-dam of claim 1 wherein an adhesive area provided with an adhesive is arranged on the foil cover between the arc members.

10. The rubber-dam of claim 1 further comprising an affixing device for affixing the rubber-dam in a desired position, wherein said affixing device comprises plastic clips for being pushed over a tooth.

11. The rubber-dam of claim 1 further comprising a rubber-dam frame arranged circularly around the affixing device.

12. The rubber-dam of claim 1 comprising a radially extensible rubber-dam frame.

13. A rubber-dam comprising a flexible cover foil for covering an oral cavity, wherein said cover foil has, in a relaxed state, the shape of a bag and at least one groove in said cover foil for marking a preferred cutting position in an incisial/occlusal area thereof.

14. A rubber dam comprising:
- a flexible cover foil for covering an oral cavity in the form of a patient's mouth, the patient's mouth having an upper and lower vestibule, upper and lower lips and two cheeks, wherein said cover foil has, in a relaxed state, the shape of a bag that is closed laterally and at a first end,
- a frame for being located outside the patient's mouth circularly around the patient's upper and lower lips, wherein an outer margin of said cover foil at a second end opposite the first end is connected to the frame, and
- arc-shaped first and second retaining members made from a firmer material than said cover foil, said first retaining member suited for being arranged in the upper vestibule of the patient's mouth and said second retaining member suited for being arranged in the lower vestibule of the patient's mouth, wherein said first and second retaining members are interconnected for generating vertical tensional forces.

15. The rubber dam of claim 14 wherein each said first and second retaining member extend along both of the patient's cheeks.

16. The rubber dam of claim 14 wherein said first and second retaining member are interconnected to form a loop.

17. The rubber-dam of claim 14 wherein at least one groove for marking a preferred cutting position is arranged in the cover foil in an incisal/occlusal area.

18. The rubber-dam of claim 14 wherein the flexible cover foil comprises a reversibly closeable opening for receiving a salvia suction tube.

19. The rubber-dam of claim 14 wherein the cover foil is at least that stable in shape that it substantially maintains its shape within the oral cavity.

20. The rubber-dam of claim 14 further comprising a flavoring.

21. A rubber-dam comprising:
- cover means comprising a flexible cover foil for covering an oral cavity in the form of a patient's mouth, the patient's mouth having an upper and lower vestibule, upper and lower lips and two cheeks, wherein said cover foil has, in a relaxed state, the shape of a bag that is closed laterally and at a first end,
- an affixing device with a, compared to the cover means, firmer holder means for pressing the cover means against the oral cavity of the patient, and a rubber-dam frame arranged circularly around the affixing device,
- wherein said affixing device comprises arc-shaped first and second retaining members made from a firmer material than said cover foil, said first retaining member suited for being arranged in the upper vestibule of the patient's mouth and said second retaining member suited for being arranged in the lower vestibule of the patient's mouth, wherein said first and second retaining members are interconnected for generating vertical tensional forces.

22. The rubber dam of claim 21 wherein each said first and second retaining member extend along both of the patient's cheeks.

23. The rubber dam of claim 21 wherein said first and second retaining member are interconnected to form a loop.

24. The rubber-dam of claim 21 wherein the holder means is elastically deformable.

25. A rubber dam comprising:
- a flexible cover foil for covering an oral cavity in the form of a patient's mouth, the patient's mouth having an upper and lower vestibule, upper and lower lips and two cheeks, wherein said cover foil has, in a relaxed state, the shape of a bag that is closed laterally and at a first end,
- a frame for being located outside the patient's mouth circularly around the patient's upper and lower lips, wherein an outer margin of said cover foil at a second end opposite the first end is connected to the frame, and
- arc-shaped first and second retaining members made from a firmer material than said cover foil, said first retaining member suited for being arranged in the upper vestibule of the patient's mouth and said second retaining member suited for being arranged in the lower vestibule of the patient's mouth, wherein said first and second retaining members extend along both of the patient's cheeks and are interconnected to a loop for generating vertical tensional forces.

26. A rubber-dam comprising:
- a flexible cover foil for covering an oral cavity of a patient's mouth with upper and lower lips,
- a frame for being located outside the patient's mouth around the patient's upper and lower lips, wherein said cover foil has, in a relaxed state, the shape of a bag that is closed laterally and at a first end, wherein an outer margin of said cover foil, at a second end opposite the first end, is connected to said frame, and
- an affixing device for affixing the rubber-dam in a desired position, wherein said affixing device comprises a holder means for pressing the cover foil against the oral cavity or gingiva or mucosa thereof, wherein the holder means is firmer than the cover foil,
- wherein a gluing area provided with an adhesive is arranged in the area of the holder means.

27. A rubber-dam comprising:
- a flexible cover foil for covering an oral cavity of a patient's mouth with upper and lower lips,
- a frame for being located outside the patient's mouth around the patient's upper and lower lips, wherein said cover foil has, in a relaxed state, the shape of a bag that is closed laterally and at a first end, wherein an outer margin of said cover foil, at a second end opposite the first end, is connected to said frame, and
- an affixing device for affixing the rubber-dam in a desired position, wherein said affixing device comprises a holder means for pressing the cover foil against the oral cavity or gingiva or mucosa thereof, wherein the holder means is firmer than the cover foil,
- wherein the holder means comprises two concentric arc members arranged at a distance from each other, and
- wherein an adhesive area provided with an adhesive is arranged on the foil cover between the arc members.

* * * * *